US006730684B1

(12) United States Patent
Miller et al.

(10) Patent No.: US 6,730,684 B1
(45) Date of Patent: May 4, 2004

(54) FAB I INHIBITORS

(75) Inventors: William H. Miller, Collegeville, PA (US); Kenneth A. Newlander, West Chester, PA (US); Mark A. Seefeld, Collegeville, PA (US); Irene N. Uzinskas, Villanova, PA (US)

(73) Assignee: Affinium Pharmaceuticals, Inc., Toronto (CA)

( * ) Notice: Subject to any disclaimer, the term of this patent is extended or adjusted under 35 U.S.C. 154(b) by 0 days.

(21) Appl. No.: 10/089,740

(22) PCT Filed: Oct. 6, 2000

(86) PCT No.: PCT/US00/27619
§ 371 (c)(1),
(2), (4) Date: Apr. 3, 2002

(87) PCT Pub. No.: WO01/26652
PCT Pub. Date: Apr. 19, 2001

Related U.S. Application Data
(60) Provisional application No. 60/158,707, filed on Oct. 8, 1999.

(51) Int. Cl.[7] .................. A61K 31/445; C07D 401/00; C07D 209/16
(52) U.S. Cl. .............. 514/323; 514/338; 514/339; 514/403; 514/415; 514/422; 546/201; 546/275.4; 548/362.5; 548/504
(58) Field of Search ................. 514/323, 338, 514/339, 403, 415, 422; 546/275.4, 201; 548/362.5, 504

(56) References Cited

U.S. PATENT DOCUMENTS

| | | | |
|---|---|---|---|
| 3,828,068 A | 8/1974 | Minieri | 548/362.5 |
| 4,154,943 A | 5/1979 | Kuehne | 546/51 |
| 4,977,159 A | 12/1990 | Sevrin et al. | 514/292 |
| 5,614,551 A | 3/1997 | Dick et al. | 514/454 |
| 5,624,941 A | 4/1997 | Barth et al. | 514/326 |
| 5,985,867 A | 11/1999 | Rodgers et al. | 514/218 |
| 6,346,391 B1 | 2/2002 | Oethinger et al. | 435/32 |
| 6,372,752 B1 | 4/2002 | Staveski et al. | 514/273 |
| 6,451,816 B1 | 9/2002 | Biedermann et al. | 514/318 |
| 6,469,046 B1 | 10/2002 | Daines et al. | 514/419 |
| 6,503,903 B1 * | 1/2003 | Miller et al. | 514/221 |
| 6,503,908 B1 * | 1/2003 | Maw | 514/243 |
| 6,559,172 B1 * | 5/2003 | Heerding et al. | 514/396 |
| 6,573,272 B1 * | 6/2003 | Miller et al. | 514/292 |
| 2003/0139377 A1 * | 7/2003 | Miller et al. | 514/64 |
| 2003/0149089 A1 * | 8/2003 | Heerding et al. | 514/396 |

FOREIGN PATENT DOCUMENTS

| | | |
|---|---|---|
| WO | WO 95/18619 | 7/1995 |
| WO | WO 96/00730 | 1/1996 |
| WO | WO 97/48696 | 12/1997 |
| WO | WO 01/26652 | 4/2001 |
| WO | WO 01/26654 * | 4/2001 |
| WO | WO 01 27103 A1 | 4/2001 |
| WO | WO 01/48248 | 7/2001 |
| WO | WO 02/42273 | 5/2002 |

OTHER PUBLICATIONS

Misztal et al., "Synthesis and Pharmacologic Properties of Pyridol Derivatives of 3–Methylaminoindole 2–Methyltryptamine and Isotryptamine", Archivum Immnologiae et Therapiae Experimentalis 1976, vol. 24, No. 6, pp. 851–852.

(List continued on next page.)

*Primary Examiner*—Ceila Chang
(74) *Attorney, Agent, or Firm*—Foley Hoag, LLP

(57) ABSTRACT

Compounds of formula (I) and (II) are disclosed

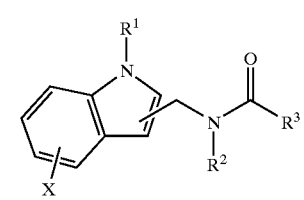
(I)

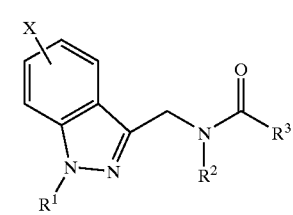

(II)

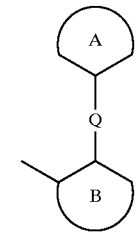

(a)

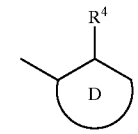

(b)

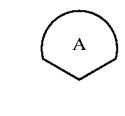

(c)

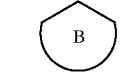

(d)

wherein, $R^1$, $R^2$, $R^3$, $R^4$, X, A, B, D and Q are as disclosed in the specification, and the compounds are FabI inhibitors useful in the treatment of bacterial infections.

17 Claims, No Drawings

OTHER PUBLICATIONS

Database CAOLDon STN, AN CA51:10524d, Hellman, et al., "N–Mannich bases (VI) condensation . . . ," *Direct Submission*. (1953).

Database CA on STN, AN 7:66733, Rosenmund, et al., "Chemistry of indole II . . . ," *Chem Ber.* (1970). vol. 103(2); pp. 496–509.

Database CAPLUS on STN, AN 1977;439214, Misztal, et al., "Synthesis and pharmacologic properties of pyridoyl . . . ," *Arch Immuno Ther Exp.* (1976). vol 24 (6) 851–862.

Himmer et al.; "Synthesis and Antibacterial in Vitro Activity of Novel Analogues of Nematophin", Bioorganic & Medicinal Chemistry Letters, 8(15): 2045–2050, (Aug. 1998).

Abou–Gharbia et al., "Psychotropic Agents: Synthesis and Antipysychotic Activity of Substituted B–Carbolines," J. Med. Chem., 30(6):1100–1115 (1987).

Ahsan et al., "Reserpine Anlogues: Synthesis of B–Carboline Derivatives," J. Chem. Soc., pp. 3928–3920 (1963).

DATABASE Crossfire Beilstein, 1966, Database accession Noo. 2819049, 2819050, XP002216033.

Miller et al., Discovery of Aminopyridine–Based Inhibitors of Bacterial Enoyl–ACP Reductase (FABI); J. Med. Chem. 2002, vol. 45, pp. 3246–3256.

Pachter et al., "The Chemistry of Hortiamine and 6–Methoxyhetsinine," J. Amer. Chem., 83:635–642 (1961).

Rehse et al., "Dopaminanaloge 1,2,3,4–Tetrahydro–B–Carboline," Arch. Pharm., 311(1):11–18 (1978).

Shoji et al., "Two Novel Alkaloids from Evodia Rutaecarpa," J. Natural Products, 52(5):1160–1162 (1989).

U.S. patent application Ser. No. 10/407,028, Methods of Agonizing and Antagonizing Fab K, filed on Apr. 4, 2003, pending.

U.S. patent application Ser. No. 09/959,172, Fab I Inhibitors, filed Apr. 19, 2000, Issued: U.S. Pat. 6,503,903.

U.S. patent application Ser. No. 10/292,687, Fab I Inhibitors, filed Nov. 12, 2002, pending: continuation of '903 patent.

U.S. patent application Ser. No. 10/339,092, Disubstituted Imidazoles Useful in the Treatment of Bacterial Compounds, filed Jan. 9, 2003, pending: continuation of the '172 patent.

U.S. patent application Ser. No. 09/980,369, Antibacterial Compounds, filed Jun. 1, 2000, Issued: U.S. Pat. 6,573,272.

U.S. patent application Ser. No. 10/429,923, Antibacterial Compounds, filed May 5, 2003, Pending: continuation of the '272 patent.

U.S. patent application Ser. No. 10/089,739, Fab I Inhibitors, filed Oct. 6, 2000, pending.

U.S. patent application Ser. No. 09/979,560, Disubstituted Imidazoles Useful in the Treatment of Bacterial Infections, filed May 24, 2000, Issued: U.S. Pat. 6,559,172.

* cited by examiner

FAB I INHIBITORS

This application claims benefit of provisional application 60/158,707 filed Oct. 8, 1999.

FIELD OF THE INVENTION

This invention relates to pharmaceutically active compounds which inhibit FabI and are useful for the treatment of bacterial infections.

BACKGROUND OF THE INVENTION

While the overall pathway of saturated fatty acid biosynthesis is similar in all organisms, the fatty acid synthase (FAS) systems vary considerably with respect to their structural organization. Vertebrates and yeast possess a FAS in which all the enzymatic activities are encoded on one or two polypeptide chains, respectively, and the acyl carrier protein (ACP) is an integral part of the complex. In contrast, in bacterial FAS, each of the reactions is catalyzed by a distinct, mono-functional enzyme and the ACP is a discrete protein. Therefore, there is considerable potential for the selective inhibition of the bacterial system by antibacterial agents.

FabI (previously designated EnvM) functions as an enoyl-ACP reductase (Bergler, et al, (1994), *J. Biol. Chem.* 269, 5493–5496) in the final step of the four reactions involved in each cycle of bacterial fatty acid biosynthesis. In this pathway, the first step is catalyzed by β-ketoacyl-ACP synthase, which condenses malonyl-ACP with acetyl-CoA (FabH, synthase III). In subsequent rounds, malonyl-ACP is condensed with the growing-chain acyl-ACP (FabB and FabF, synthases I and II, respectively). The second step in the elongation cycle is ketoester reduction by NADPH-dependent β-ketoacyl-ACP reductase (FabG). Subsequent dehydration by β-hydroxyacyl-ACP dehydrase (either FabA or FabZ) leads to trans-2-enoyl-ACP, which in turn is converted to acyl-ACP by NADH-dependent enoyl-ACP reductase (FabI). Further rounds of this cycle, adding two carbon atoms per cycle, eventually lead to palmitoyl-ACP (16C), where upon the cycle is stopped largely due to feedback inhibition of FabI by palmitoyl-ACP (Heath, et al, (1996), *J. Biol. Chem.* 271, 1833–1836). Thus, FabI is a major biosynthetic enzyme and is a key regulatory point in the overall synthetic pathway of bacterial fatty acid biosynthesis. Therefore, FabI is an ideal target for antibacterial intervention.

Studies have shown that diazaborine antibiotics inhibit fatty acid, phospholipid and lipopolysaccharide (LPS) biosynthesis and that the antibacterial target of these compounds is FabI. For example, derivative 2b18 from Grassberger, et al (1984) *J. Med Chem* 27 947–953 has been reported to be a non-competitive inhibitor of FabI (Bergler, et al, (1994), *J. Biol. Chem.* 269, 5493–5496). Also, plasmids containing the FabI gene from diazaborine resistant *S. typhimurium* conferred diazaborine resistance in *E. coli* (Turnowsky, et al, (1989), *J. Bacteriol.*, 171, 6555–6565). Furthermore, inhibition of FabI either by diazaborine or by raising the temperature in a FabI temperature sensitive mutant is lethal. These results demonstrate that FabI is essential to the survival of the organism (Bergler, et al, (1994), *J. Biol. Chem.* 269, 5493–5496).

Recent studies have shown that FabI is also the target for the broad spectrum antibacterial agent triclosan (McMurry, et al, (1998) *Nature* 394, 531–532). A crystal structure of the *E. Coli* FabI complexed with NAD and triclosan shows that triclosan acts as a site-directed, very potent inhibitor of FabI by mimicking its natural substrate (Levy, et al, (1999) *Nature* 398, 383–384). Ward. et al ((1999) *Biochem.* 38, 12514–12525) have shown that there is no evidence for the formation of a covalent complex between FabI and triclosan, which would be analogous to the diazaborines: triclosan differs from these compounds in that it is a reversible inhibitor of FabI. The structural data for the complex of FabI with NAD and triclosan provides important information about FabI as a therapeutic target.

Importantly, it has now been discovered that certain compounds are FabI inhibitors and have antibacterial activity, and, therefore, may be useful for the treatment of bacterial infections in mammals, particularly in man.

SUMMARY OF THE INVENTION

This invention comprises compounds of the formula (I), as described hereinafter, which inhibit FabI and are useful in the treatment of bacterial infections.

This invention is also a pharmaceutical composition comprising a compound according to formula (I) and a pharmaceutically acceptable carrier.

This invention is also a method of treating bacterial infections by inhibiting FabI. In a particular aspect, the compounds of this invention are useful as antibacterial agents.

DETAILED DESCRIPTION

This invention comprises compounds of formula (I) and (II):

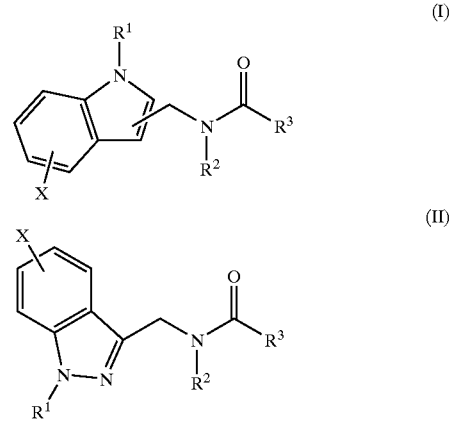

wherein:

$R^1$ is H or $C_{1-4}$alkyl;
$R^2$ is $C_{1-4}$alkyl;
$R^3$ is

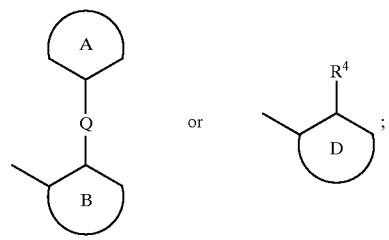

Q is a single bond, —O—, —S—, —NH—, —$CH_2$—, or —$CH_2CH_2$—;

$R^4$ is $C_{1-6}$alkyl, $OC_{1-6}$alkyl, OH, $CF_3$ or piperidinyl;

(A) is a five- or six-membered heteroaromatic ring or a six-membered aromatic ring unsubstituted or substituted by $R^5$;

(B) is a five- or six-membered heteroaromatic ring or a six-membered aromatic ring unsubstituted or substituted by $R^6$;

(D) is a five- or six-membered heteroaromatic ring or a six-membered aromatic ring unsubstituted or substituted by $R^6$;

$R^5$ is OR' or NR'C(O)R';
$R^6$ is OR' or N(R')$_2$;
X is H, $C_{1-4}$alkyl, OR', SR', CN, N(R')$_2$, CH$_2$N(R')$_2$, NO$_2$, CF$_3$, CO$_2$R', CON(R')$_2$, COR', NR'C(O)R', F, Cl, Br, I or —S(O)$_r$CF$_3$;
R' is H, $C_{1-6}$alkyl or —$C_{0-6}$alkyl-Ar; and
r is 0, 1 or 2;
or a pharmaceutically acceptable salt thereof.

Also included in this invention are pharmaceutically acceptable addition salts and complexes of the compounds of this invention. In cases wherein the compounds of this invention may have one or more chiral centers, unless specified, this invention includes each unique racemic compound, as well as each unique nonracemic compound.

In cases in which compounds have unsaturated carbon-carbon double bonds, both the cis (Z) and trans (E) isomers are within the scope of this invention. In cases wherein compounds may exist in tautomeric forms, such as keto-enol tautomers, such as and each tautomeric form is contemplated as being included within this invention, whether existing in equilibrium or locked in one form by appropriate substitution with R'. The meaning of any substituent at any one occurrence is independent of its meaning, or any other substituent's meaning, at any other occurrence.

Also included in this invention are prodrugs of the compounds of this invention. Prodrugs are considered to be any covalently bonded carriers which release the active parent drug according to formula (I) in vivo.

The compounds of formula (I) inhibit FabI. Inhibition of this enzyme is useful in the treatment of bacterial infections. Also, the compounds of this invention may be useful as antifungal agents. Additionally, the compounds may be useful in combination with known antibiotics.

With respect to formula (I) and (II), this invention preferably includes compounds of formula (Ia) and (IIa):

(Ia)

(IIa)

in which $R^3$ is as defined for formula (I) and (II) compounds.

Suitably, with respect to formula (I) and (II), $R^3$ is:

Preferably, (A) is 2-, 3- or 4-pyridyl, 2- or 3-furanyl, 2- or 3-thiophenyl, thiazolyl, phenyl or phenyl substituted by $OC_{1-4}$alkyl or NHC(O)$C_{1-4}$alkyl. Most preferably, (A) is 3- or 4-pyridyl, 3-furanyl, 3-thiophenyl, phenyl or phenyl substituted by OCH$_3$ or NHC(O)CH$_3$. Also, preferably, (B) is 2-, 3- or 4-pyridyl, phenyl or phenyl substituted by OH or NH$_2$. Most prefarably,

is phenyl or 2-pyridyl.

Suitably, with respect to formula (I) and (II), $R^3$ is:

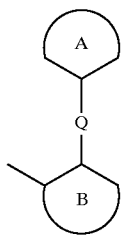

in which Q is a single bond, —O— or CH$_2$CH$_2$—. Preferably, Q is a single bond.

Suitably, with respect to formula (I), $R^3$ is:

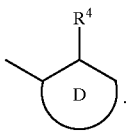

Preferably,

is phenyl unsubstituted or substituted by OH, NH$_2$ or N(CH$_3$)$_2$ and $R^4$ is $C_{1-4}$alkyl, OC$_{1-4}$alkyl, OH, CF$_3$ or piperidinyl.

Representative of the novel compounds of this invention are the compounds of the examples hereinafter.

Abbreviations and symbols commonly used in the peptide and chemical arts are used herein to describe the compounds of this invention. In general, the amino acid abbreviations follow the IUPAC-IUB Joint Commission on Biochemical Nomenclature as described in *Eur. J. Biochem.*, 158, 9 (1984).

$C_{1-4}$alkyl as applied herein means an optionally substituted alkyl group of 1 to 4 carbon atoms, and includes methyl, ethyl, n-propyl, isopropyl, n-butyl, isobutyl and t-butyl. $C_{1-6}$alkyl additionally includes pentyl, n-pentyl, isopentyl, neopentyl and hexyl and the simple aliphatic isomers thereof. $C_{0-4}$alkyl and $C_{0-6}$alkyl additionally indicates that no alkyl group need be present (e.g., that a covalent bond is present).

Any $C_{1-4}$alkyl or $C_{1-6}$alkyl may be optionally substituted with the group $R^x$, which may be on any carbon atom that results in a stable structure and is available by conventional synthetic techniques. Suitable groups for $R^x$ are $C_{1-4}$alkyl, OR', SR', CN, N(R')$_2$, CH$_2$N(R')$_2$, —NO$_2$, —CF$_3$, —CO$_2$R'—CON(R')$_2$, —COR'—NR'C(O)R', F, Cl, Br, I, or —S(O),CF$_3$, wherein R' and r are as defined for formula (I) compounds.

Halogen or halo means F, Cl, Br, and I.

Ar, or aryl, as applied herein, means phenyl or naphthyl, or phenyl or naphthyl substituted by one to three substituents, such as those defined above for alkyl, or substituted by methylenedioxy.

Het, or heterocycle, indicates an optionally substituted five or six membered monocyclic ring, or a nine or ten-membered bicyclic ring containing one to three heteroatoms chosen from the group of nitrogen, oxygen and sulfur, which are stable and available by conventional chemical synthesis. Illustrative heterocycles are benzofuryl, benzimidazolyl, benzopyranyl, benzothienyl, furyl, imidazolyl, indolinyl, morpholinyl, piperidinyl, piperazinyl, pyrrolyl, pyrrolidinyl, tetrahydropyridinyl, pyridinyl, thiazolyl, thienyl, quinolinyl, isoquinolinyl, and tetra- and perhydro-quinolinyl and isoquinolinyl. Any accessible combination of up to three substituents on the Het ring, such as those defined above for alkyl, that are available by chemical synthesis and are stable are within the scope of this invention.

Certain radical groups are abbreviated herein. t-Bu refers to the tertiary butyl radical, Boc refers to the t-butyloxycarbonyl radical, Fmoc refers to the fluorenylmethoxycarbonyl radical, Ph refers to the phenyl radical, Cbz refers to the benzyloxycarbonyl radical, Bn refers to the benzyl radical, Me refers to methyl, Et refers to ethyl, Ac refers to acetyl, Alk refers to $C_{1-4}$alkyl, Nph refers to 1- or 2-naphthyl and cHex refers to cyclohexyl. Tet refers to 5-tetrazolyl.

Certain reagents are abbreviated herein. DCC refers to dicyclohexylcarbodiimide, DMAP refers to dimethylaminopyridine, EDC refers to 1-(3-dimethylaminopropyl)-3-ethylcarbodiimide, hydrochloride, HOBt refers to 1-hydroxybenzotriazole, THF refers to tetrahydrofuran, DIEA refers to diisopropylethylamine, DEAD refers to diethyl azodicarboxylate, PPh$_3$ refers to triphenylphosphine, DIAD refers to diisopropyl azodicarboxylate, DME refers to dimethoxyethane, DMF refers to dimethylformamide, NBS refers to N-bromosuccinimide, Pd/C refers to a palladium on carbon catalyst, PPA refers to polyphosphoric acid, DPPA refers to diphenylphosphoryl azide, BOP refers to benzotriazol-1-yloxy-tris(dimethyl-amino)phosphonium hexafluorophosphate, HF refers to hydrofluoric acid, TEA refers to triethylamine, TFA refers to trifluoroacetic acid, PCC refers to pyridinium chlorochromate.

Generally, the compounds of formula (I) and (II) are prepared by:

(i) reacting a compound of formula (III) with a compound of formula (IV):

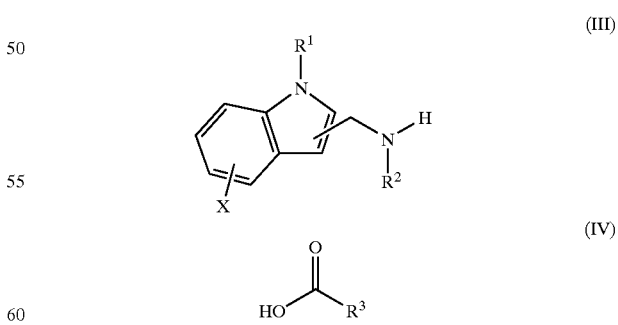

wherein $R^1$, $R^2$, $R^3$ and X are as defined in formula (I), with any reactive functional groups protected, in the presence of EDC and HOBT; or (ii) reacting a compound of formula (V) with a compound of formula (IV):

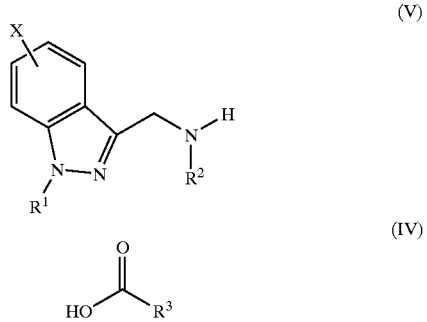

wherein $R^1$, $R^2$, $R^3$ and X are as defined in formula (I), with any reactive functional groups protected, in the presence of EDC and HOBT;

and thereafter removing any protecting groups, and optionally forming a pharmaceutically acceptable salt.

In particular, compounds of the formula (I) and (II) are prepared by the general methods described in Schemes hereinafter.

amine, for instance 1-methyl-2-(methylaminomethyl)indole, in a suitable solvent such as DMF, $CH_2Cl_2$, or $CH_3CN$, to afford I-2. Depending on whether acid neutralization is required, an added base, such as triethylamine ($Et_3N$), diisopropylethylamine (($i$-$Pr)_2NEt$), or pyridine, may be used. Many additional methods for converting a carboxylic acid to an amide are known, and can be found in standard reference books, such as "Compendium of Organic Synthetic Methods", Vol. I–VI (published by Wiley-Interscience), or Bodansky, "The Practice of Peptide Synthesis" (published by Springer-Verlag). The resulting haloarylcarboxamide 1–2 is reacted with an appropriate boronic acid derivative, such as furan-3-boronic acid, to afford I-3 in a Suzuki-type reaction (*Synth. Commun.* 1981, 11, 513; for a review, see Martin, A. R.; Yang, Y. *Acta Chem. Scand.* 1993, 47, 221). This reaction is generally mediated by tetrakis(triphenylphosphine)palladium(0), although a wide variety of palladium catalysts can be used, including palladium acetate, palladium acetate in the presence of tri(ortho-tolyl)phosphine, bis(triphenylphosphine)palladium (II) chloride, 1,4-bis(diphenylphosphinobutane)palladium (II) chloride, bis(acetonitrile)palladium(II) chloride, bis(dibenzylideneacetone)palladium(0), and palladium on carbon in the presence of triphenylphosphine. The reaction requires a base as an acid scavenger, and generally aqueous sodium carbonate ($Na_2CO_3$) is used. However, other bases, such as sodium hydrogen carbonate, potassium carbonate, cesium carbonate, cesium fluoride, and triethylamine can be used. Typically, water-miscible neutral solvents, including DME, THF, and DMF, are preferred.

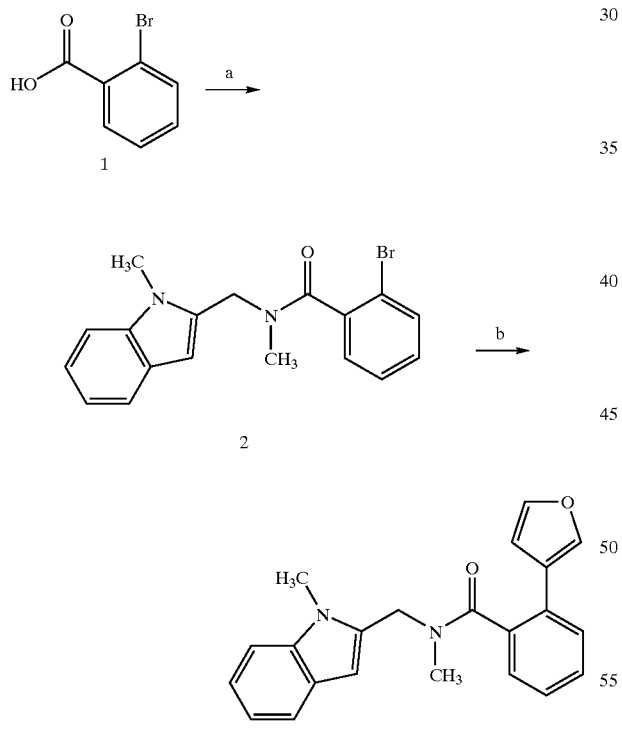

Scheme I

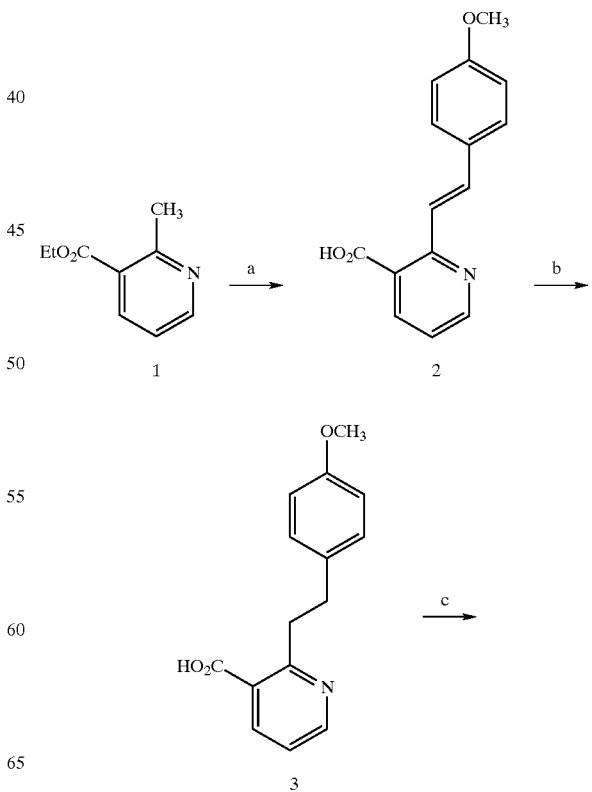

Scheme II (a) 1-methyl-2-(methylaminomethyl)indole, EDC, HOBt.$H_2O$, $Et_3N$, DMF; (b) furan-3-boronic acid. Pd($PPh_3$)$_4$, $Cs_2CO_3$, DME, $H_2O$.

A suitable 2-haloarylcarboxylic acid, for instance 2-bromobenzoic acid (I-1), is converted to an activated form using, for example, EDC and HOBt, or $SOCl_2$, and the activated form is subsequently reacted with an appropriate -continued

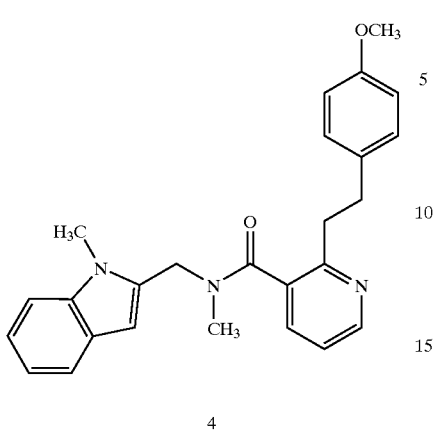

4

(a) para-anisaldehyde, NaH, tert-BuOH, DMF; (b) H₂, Pd/C, NaOH, H₂O; (c) 1-methyl-2-(methylaminomethyl)indole, EDC, HOBt.H₂O, (i-Pr)₂NEt, DMF.

According to the general procedure of Brenner et al. (*J. Het. Chem.* 1982, 19, 897–900), a suitable 2-methylnicotinic ester, for instance ethyl 2-methylnicotinate (II-1), is reacted with an aromatic aldehyde, such as para-anisaldehyde, to afford I-2. The reaction is mediated by strong base, typically sodium tert-butoxide, and is conducted in a polar solvent, generally DMF. Reduction of the olefin group of I-2 is conveniently accomplished by hydrogenation as described by van der Stelt, et al. (*Arzneim.-Forsch.* 1968, 18, 756–758). The reaction is conducted under basic conditions in the presence of a palladium catalyst, generally palladium on activated charcoal. Alkali metal hydroxides, such as sodium hydroxide or potassium hydroxide, are the preferred bases, and the reaction is typically conducted in H₂O, although an aqueous hydroxylic solvent, such as aqueous MeOH, EtOH, or i-PrOH, may also be used. The resulting acid, II-3, is converted to II-4 by the methods described in Scheme I.

Scheme III

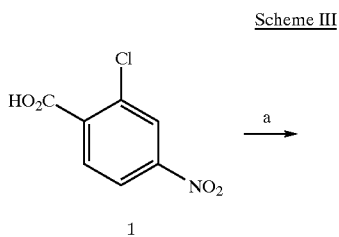

1

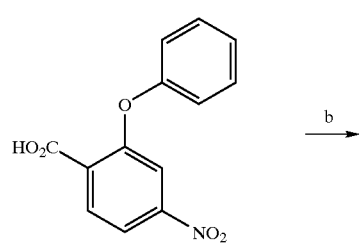

2

-continued

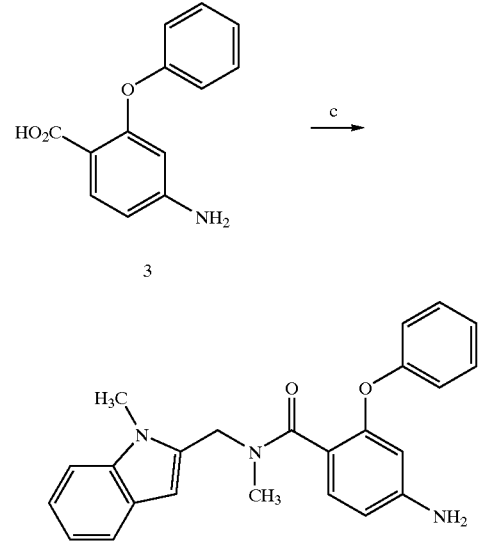

(a) phenol, NaOMe, MeOH, then Cu, DMA; (b) H₂, Pd/C, MeOH; (c) 1-methyl-2-(methylaminomethyl)indole, EDC, HOBt.H₂O, Et₃N, DMF.

A suitable 2-halobenzoic acid derivative, for instance 2-chloro-4-nitrobenzoic acid (III-2), reacts with an appropriate alcohol, for example phenol, to afford an ether derivative such as III-2. The reaction is mediated by copper powder, and is typically conducted in a high-boiling, polar, aprotic solvent, such as N,N-dimethylacetamide (DMA). The alcohol derivative is oftentimes converted to the corresponding alkoxide by deprotonation with a suitable base. Typical bases include sodium hydride (NaH) in THF, DMF, or DMA (or mixtures thereof), or sodium methoxide (NaOMe) in methanol. The nitro group of III-2 can be reduced conveniently by hydrogenation over a palladium metal catalyst, typically palladium on activated carbon (Pd/C). Suitable solvents for this reaction include MeOH, EtOH, EtOAc, AcOH, or mixtures thereof. Other methods for the reduction of nitro groups to the corresponding amine are known to those of skill in the art, and can be found in standard reference volumes, such as Compendium of Organic Synthetic Methods (Wiley-Interscience). The resulting derivative III-3 is converted to III-4 as described in Scheme I.

Scheme IV

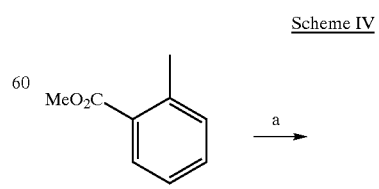

1

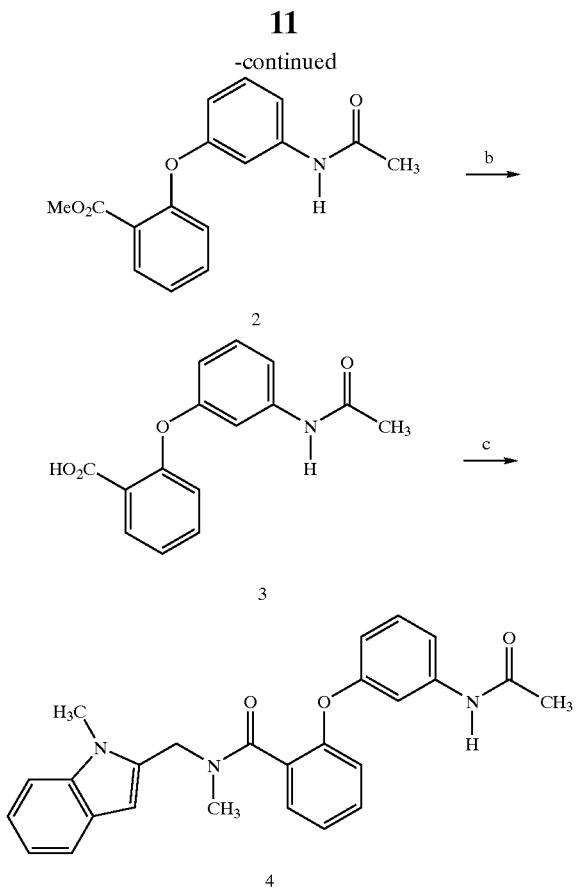

(a) 3-(acetylamino)phenol, Cu$_2$O, DMA; (b) NaOH, dioxane, H$_2$O, then HCl; (c) 1-methyl-2-(methylaminomethyl)indole, EDC, HOBt.H$_2$O, Et$_3$N, DMF.

Alternatively, a suitable 2-halobenzoic acid derivative, for instance methyl 2-iodobenzoate (IV-1), reacts with an appropriate alcohol, for example 3-(acetylamino)phenol, in the presence of a copper(I) salt, preferably copper(I) oxide (Cu$_2$O), to afford the ether derivative IV-2. A polar, aprotic solvent such as N,N-dimethylacetamide (DMA) is preferred. The methyl ester of IV-2 is hydrolyzed using aqueous base, for example, LiOH or NaOH in aqueous dioxane, THF, methanol or ethanol, and the intermediate carboxylate salt is acidified with a suitable acid, for instance TFA or HCl, to afford the carboxylic acid IV-3, which is converted to IV-4 as described in Scheme I.

Amide coupling reagents as used herein denote reagents which may be used to form peptide bonds. Typical coupling methods employ carbodiimides, activated anhydrides and esters and acyl halides. Reagents such as EDC, DCC, DPPA, PPA, BOP reagent, HOBt, N-hydroxysuccinimide and oxalyl chloride are typical.

Acid addition salts of the compounds are prepared in a standard manner in a suitable solvent from the parent compound and an excess of an acid, such as hydrochloric, hydrobromic, hydrofluoric, sulfuric, phosphoric, acetic, trifluoroacetic, maleic, succinic or methanesulfonic. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as Li$^+$, Na$^+$, K$^+$, Ca$^{++}$, Mg$^{++}$ and NH$_4^+$ are specific examples of cations present in pharmaceutically acceptable salts.

This invention also provides a pharmaceutical composition which comprises a compound according to formula (I) or (II) and a pharmaceutically acceptable carrier. Accordingly, the compounds of formula (I) or (II) may be used in the manufacture of a medicament. Pharmaceutical compositions of the compounds of formula (I) or (II) prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these compounds may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients, such as cocoa butter, glycerin, gelatin or polyethylene glycols, and molded into a suppository.

For topical administration, the compounds of this invention may be combined with diluents to take the form of ointments, gels, pastes, creams, powders or sprays. The compositions which are ointments, gels, pastes or creams contain diluents, for example, animal and vegetable fats, waxes, paraffins, starch, tragacanth, cellulose derivatives, polyethylene glycols, silicones, bentonites, silicic acid, talc and zinc oxide, or mixtures of these substances. The compositions which are powders or sprays contain diluents, for example, lactose, talc, silicic acid, aluminum hydroxide, calcium silicate and polyamide powder, or mixtures of these substances. Additionally, for topical ophthalmologic administration, the typical carriers are water, mixtures of water and water miscible solvents, such as lower alkanols or vegetable oils, and water-soluble non-toxic polymers, for example cellulose derivatives, such as methyl cellulose.

The compounds described herein are inhibitors of FabI, and are useful for treating bacterial infections. For instance, these compounds are useful for the treatment of bacterial infections, such as, for example, infections of upper respiratory tract (e.g. otitis media, bacterial tracheitis, acute epiglottitis, thyroiditis), lower respiratory (e.g. empyema, lung abscess), cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal and orbital cellulitis, darcryocystitis), kidney and urinary tract (e.g. epididymitis, intrarenal and perinephric abscess, toxic shock syndrome), skin (e.g. impetigo, folliculitis, cutaneous abscesses, cellulitis, wound infection, bacterial myositis), and bone and joint (e.g. septic arthritis, osteomyelitis). Also, the compounds of this invention may be useful as antifungal agents. Additionally, the compounds may be useful in combination with known antibiotics.

The compounds of this invention are administered to the patient, in a manner such that the concentration of drug is sufficient to treat bacterial infections. The pharmaceutical composition containing the compound is administered at an oral dose of between about 10 mg to about 1000 mg, taken once or several times daily, in a manner consistent with the condition of the patient. Preferably, the oral dose would be about 50 mg to about 500 mg, although the dose may be varied depending upon the age, body weight and symptoms of the patient. For acute therapy, parenteral administration is preferred. An intravenous infusion of the compound of formula (I) or (II) in 5% dextrose in water or normal saline, or a similar formulation with suitable excipients, is most effective, although an intramuscular bolus injection is also useful. The precise level and method by which the compounds are administered is readily determined by one skilled in the art.

The compounds may be tested in one of several biological assays to determine the concentration of compound which is required to have a given pharmacological effect.

Cloning of S. aureus FabI:

The fabI gene was cloned from the chromosomal DNA of S. aureus strain WCUH29 using the polymerase chain reaction. Amplification was performed using Taq DNA polymerase (BRL) and the following primers: 5'-CGCCTCGAGATGTFAAATCTGAAAACAAAACATATGT-3' and 5'-CGCGGATCCAATCAAGTCAGGTGAAATATCCA-3' (XhoI and BamHI sites underlined). The resulting fragment was then digested with XhoI and BamHII and ligated into XhoI- and BamHII-digested expression vector pET-16b (Novagen), producing pET-His$_{10}$-fabI. The gene sequence of fabI was confirmed by automated cycle sequencing using an Applied Biosystems model 377 machine. The untagged version of pET-fabI was constructed by digesting pET-His$_{10}$-fabI with NcoI and NdeI to remove a 97 bp fragment encoding the His 10 tag, the factor Xa cleavage site and the first 8 amino acids of FabI, and replacing it with a linker encoding the first 8 amino acids of FabI plus a glycine residue between the initiator methionine and the lysine at position 2. This plasmid was called pET-fabI. The linker was made by annealing the following two oligonucleotides: 5'-CATGGGCTTAAATCTTGAAAACAAAACA-3' and 5'-TATGTTTTGTTTTCAAGATTTAAGCC-3'. The linker sequence in pET-fabI was confirmed by dideoxy sequencing. Only native FabI was used for compound evaluation. For overproduction of native FabI, plasmid pET-fabI was transformed into BL21(DE3) (Novagen) cells, to form strain BL21(DE3):pET-fabI.

Purification of S. aureus FabI

S. aureus FabI was expressed as soluble protein to 10% of total cell protein, 400 g cells being recovered from 15 L fermentation in tryptone phosphate medium. The cells were lysed and the sample centrifuged. The resulting supernatant was filtered and purified using three consecutive chromatography columns: ion-exchange (Sourse 15Q), dye-affinity (Blue sepharose), and size exclusion chromatography columns (Superose 12). After each column the FabI containing fractions were pooled, concentrated, and checked for purity and biological activity.

Cloning of E. coli FabI:

A PCR fragment of correct size for E. coli FabI was PCR amplified from E. coli chromosomal DNA, subcloned into the TOPO TA cloning vector, and verified by colony PCR+ restriction endonuclease analysis. The presumptive E. coli FabI PCR fragment was subcloned into the expression vector pBluePet. The FabI clone was transformed into E. coli strain BL21(DE3). Small Scale expression studies show an over-expressed protein band of correct molecular weight (~28 Kda) for E. coli FabI clearly visible following Coomassie staining of SDS PAGE gels. DNA sequencing of the E. coli FabI expression constructs illustrated that no errors were apparent. N' terminal amino acid sequencing has confirmed the over-expressed protein band to be E. coli FabI.

Purification of E. coli FabI

E. coli FabI was expressed as soluble protein to 15% of total cell protein, 120 g cells being recovered from 3 L fermentation in shake flasks in modified terrific broth. The cells were lysed and the sample centrifuged. The resulting supernatant was filtered and purified using three consecutive chromatography columns: ion-exchange (Sourse 15Q), dye-affinity (blue sepharose), and size exclusion (superose 12). After each column the FabI containing fractions were pooled, concentrated and checked for purity and biological activity.

S. aureus FabI Enzyme Inhibition Assay (NADH):

Assays were carried out in half-area, 96-well microtitre plates. Compounds were evaluated in 50-uL assay mixtures containing 100 mM NaADA, pH 6.5 (ADA=N-[2-acetamido]-2-iminodiacetic acid), 4% glycerol, 0.25 mM crotonoyl CoA, 1 mM NADH, and an appropriate dilution of S. aureus FabI. Inhibitors were typically varied over the range of 0.01–10 uM. The consumption of NADH was monitored for 20 minutes at 30° C. by following the change in absorbance at 340 nm. Initial velocities were estimated from an exponential fit of the non-linear progress curves represented by the slope of the tangent at t=0 min. IC$_{50}$'s were estimated from a fit of the initial velocities to a standard, 4-parameter model and are typically reported as the mean±S.D. of duplicate determinations. Triclosan, a commercial antibacterial agent and inhibitor of FabI, is currently included in all assays as a positive control. Compounds of this invention have IC$_{50}$'s from about 1.50 micromolar to about 0.15 micromolar.

S. aureus FabI Enzyme Inhibition Assay (NADPH):

Assays were carried out in half-area, 96-well microtitre plates. Compounds were evaluated in 150-uL assay mixtures containing 100 mM NaADA, pH 6.5 (ADA=N-[2-acetamido]-2-iminodiacetic acid), 4% glycerol, 0.25 mM crotonoyl CoA, 50 uM NADPH, and an appropriate dilution of S. aureus FabI. Inhibitors were typically varied over the range of 0.01–10 uM. The consumption of NADPH was monitored for 20 minutes at 30° C. by following the change in absorbance at 340 nm. Initial velocities were estimated from an exponential fit of the non-linear progress curves represented by the slope of the tangent at t=0 min. IC$_{50}$'s were estimated from a fit of the initial velocities to a standard, 4-parameter model and are typically reported as the mean±S.D. of duplicate determinations. Triclosan, a commercial antibacterial agent and inhibitor of FabI, is currently included in all assays as a positive control.

E. coli FabI Enzyme Inhibition Assay:

Assays were carried out in half-area, 96-well microtitre plates. Compounds were evaluated in 150-uL assay mixtures containing 100 mM NaADA, pH 6.5 (ADA=N-[2-acetamido]-2-iminodiacetic acid), 4% glycerol, 0.25 mM crotonoyl CoA, 50 uM NADH, and an appropriate dilution of E. coli FabI. Inhibitors were typically varied over the range of 0.01–10 uM. The consumption of NADH was monitored for 20 minutes at 30° C. by following the change in absorbance at 340 nm. Initial velocities were estimated from an exponential fit of the non-linear progress curves represented by the slope of the tangent at t=0 min. $IC_{50}$'s were estimated from a fit of the initial velocities to a standard, 4-parameter model and are typically reported as the mean±S.D. of duplicate determinations. Triclosan, a commercial antibacterial agent and inhibitor of FabI, is currently included in all assays as a positive control. Compounds of this invention have $IC_{50}$'s from about 20.0 micromolar to about 2.0 micromolar.

Preparation and Purification of Crotonoyl-ACP:

Reactions contained 5 mg/mL E. coli apo-ACP, 0.8 mM crotonoyl-CoA (Fluka), 10 mM $MgCl_2$, and 30 uM S. pneumoniae ACP synthase in 50 mM NaHEPES, pH 7.5. The mixture was gently mixed on a magnetic stirrer at 23° C. for 2 hr, and the reaction was terminated by the addition of 15 mM EDTA. The reaction mixture was filtered through a 0.2 micron filter (Millipore) and applied to a MonoQ column (Pharmacia) equilibrated with 20 mM Tris-Cl, pH 7.5. The column was washed with buffer until all non-adherent material was removed (as observed by UV detection), and the crotonoyl-ACP was eluted with a linear gradient of 0 to 400 mM NaCl.

S. aureus FabI Enzyme Inhibition Assay Using Crotonoyl-ACP:

Assays are carried out in half-area, 96-well microtitre plates. Compounds are evaluated in 150 uL assay mixtures containing 100 mM NaADA, pH 6.5 (ADA=N-(2-acetamido)-2-iminodiacetic acid), 4% glycerol, 25 uM crotonoyl-ACP, 50 uM NADPH and an appropriate dilution of S. aureus FabI (approximately 20 nM). Inhibitors are typically varied over the range of 0.01–10 uM. The consumption of NADPH is monitored for 20 minutes at 30° C. by following the change in absorbance at 340 nm. Initial velocities are estimated from a linear fit of the progress curves. IC50's are estimated from a fit of the initial velocities to a standard, 4-parameter model (Equation 1) and are typically reported as the mean±S.D. of duplicate determinations. The apparent Ki is calculated from Equation 2 assuming the inhibition is competitve with crotonoyl-ACP.

$v=\text{Range}/(1+[I]/\text{IC}50)s+\text{Background}$    Equation 1:

$Ki(app)=IC50/(1+[S]/Ks)$    Equation 2:

Antimicrobial Activity Assay:

Whole-cell antimicrobial activity was determined by broth microdilution using the National Committee for Clinical Laboratory Standards (NCCLS) recommended procedure, Document M7-A4, "Methods for Dilution Susceptibility Tests for Bacteria that Grow Aerobically". The compound was tested in serial two-fold dilutions ranging from 0.06 to 64 mcg/mL. Test organisms were selected from the following laboratory strains: Staphylococcus aureus Oxford, Staphylococcus aureus WCUH29, Streptococcus pneumoniae ERY2, Streptococcus pneumoniae 1629, Streptococcus pneumoniae N 1387, Enterococcus faecalis I, Enterococcus faecalis 7, Haemophilus influenzae Q1, Haemophilus influenzae NEMC1, Moraxella Catarrhalis 1502, Escherichia coli 7623 AcrABEFD+, Escherichia coli 120 AcrAB−, Escherichia coli MGJ655, Escherichia coli MG1658. The minimum inhibitory concentration (MIC) was determined as the lowest concentration of compound that inhibited visible growth. A mirror reader was used to assist in determining the MIC endpoint.

One skilled in the art would consider any compound with a MIC of less than 256 µg/mL to be a potential lead compound. Preferably, the compounds used in the antimicrobial assays of the present invention have a MIC value of less than 128 µg/mL. Most preferably, said compounds have a MIC value of less than 64 µg/mL.

The examples which follow are intended in no way to limit the scope of this invention, but are provided to illustrate how to make and use the compounds of this invention. Many other embodiments will be readily apparent to those skilled in the art.

EXAMPLES

General

Proton nuclear magnetic resonance ($^1$H NMR) spectra were recorded at either 250, 300, 360, or 400 MHz, and chemical shifts are reported in parts per million (δ) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. $CDCl_3$ is deuteriochloroform, $DMSO-d_6$ is hexadeuteriodimethylsulfoxide, and $CD_3OD$ is tetradeuteriomethanol. Mass spectra were obtained using electrospray (ES) ionization techniques. Elemental analyses were performed by Quantitative Technologies Inc., Whitehouse, N.J. Melting points were obtained on a Thomas-Hoover melting point apparatus and are uncorrected. All temperatures are reported in degrees Celsius. Analtech Silica Gel GF and E. Merck Silica Gel 60 F-254 thin layer plates were used for thin layer chromatography. Flash chromatography was carried out on E. Merck Kieselgel 60 (230–400 mesh) silica gel. Analytical HPLC was performed on Beckman chromatography systems. Preparative HPLC was performed using Gilson chromatography systems. ODS refers to an octadecylsilyl derivatized silica gel chromatographic support. YMC ODS-AQ® is an ODS chromatographic support and is a registered trademark of YMC Co. Ltd., Kyoto, Japan. PRP-1® is a polymeric (styrene-divinylbenzene) chromatographic support, and is a registered trademark of Hamilton Co., Reno, Nev. Celite® is a filter aid composed of acid-washed diatomaceous silica, and is a registered trademark of Manville Corp., Denver, Colo.

Preparation 1

Preparation of 1-Methyl-2-(methylaminomethyl)indole a) Ethyl 1-Methylindole-2-carboxylate NaH (60% dispersion in mineral oil, 8.02 g, 200.49 mmole) was washed with hexanes, then was suspended in dry DMF (530 mL). Solid ethyl indole-2-carboxylate (25.29 g, 133.66 mmole) was added portionwise over 5–10 min. allowing gas evolution to subside between additions. When the addition was complete, the yellow mixture was stirred for 15 min, then methyl iodide (42 mL, 668.3 mmole) was added all at once. The reaction was exothermic, and the internal temperature rose to 40–45° C. After 1 hr, the reaction was quenched with 10% $NH_4Cl$ (100 mL) and concentrated on the rotavap (high vacuum). The residue was partitioned between $Et_2O$ (500 mL) and $H_2O$ (100 mL), and the layers were separated. The Et$_2$O layer was washed with H$_2$O (100 mL), dried (MgSO$_4$), and concentrated to leave the title compound (27.10 g, quantitative) as a light yellow solid. This was used without further purification: TLC (10% EtOAc/hexanes) Rf=0.39.

b) N,1-Dimethylindole-2-carboxamide

A suspension of ethyl 1-methylindole-2-carboxylate (27.10 g, 133.34 mmole) in 40% aqueous CH$_3$NH$_2$ (300 mL) and MeOH (30 mL) was stirred at RT. A solid tended to gradually creep up the walls of the flask, and was washed down periodically with MeOH. The flask was tightly stoppered to keep the material inside the flask. As the reaction proceeded, the solid dissolved, but eventually the product began to precipitate. The reaction was stirred at RT for 5 days, then was concentrated to remove approximately 200 mL of the solvent. The remaining residue was diluted with H$_2$O (300 mL), and the solid was collected by suction filtration and washed with H$_2$O. Drying at 50–60° C. in high vacuum left the title compound (23.45 g, 93%) as a faintly yellow solid: $^1$H NMR (300 MHz, CDCl$_3$) δ 7.63 (d, J=8.0 Hz, 1H), 7.27–7.43 (m, 2H), 7.10–7.20 (m, 1H), 6.80 (s, 1H), 6.10–6.30 (m, 1H), 4.06 (s, 3H), 3.01 (d, J=4.9 Hz, 3H).

c) 1-Methyl-2-(methylaminomethyl)indole

A 3-liter 3-necked roundbottom flask equipped with overhead stirring was charged with N,1-dimethylindole-2-carboxamide (23.45 g, 124.58 mmole) and anhydrous THF (170 mL). The solution was stirred while a solution of LiAlH$_4$ in THF (1.0 M, 250 mL, 250 mmole) was added via syringe. Gas was evolved during the addition of the first 50 mL of LiAlH$_4$ solution. When the addition was complete, the resulting light yellow solution was heated at gentle reflux. After 23 hr, the reaction was cooled in ice and quenched by the sequential dropwise addition of H$_2$O (9.5 mL), 15% NaOH (9.5 mL). and H$_2$O (28.5 mL). The mixture was stirred for 15 min, then was filtered through celite®, and the filter pad was washed thoroughly with THF. The filtrate was concentrated and the residue was flash chromatographed on silica gel (10% MeOH/CHCl$_3$ containing 0.5% conc. NH$_4$OH). The title compound (20.17 g, 93%) was obtained as a light yellow oil: $^1$H NMR (300 MHz, CDCl$_3$) δ 7.56 (d, J=7.8 Hz, 1H), 7.02–7.35 (m, 3H), 6.38 (s, 1H), 3.88 (s, 2H), 3.75 (s, 3H), 2.49 (s, 3H).

Preparation 2

Preparation of 2-[2-(4-Methoxyphenyl)ethyl]nicotinic Acid a) 2-[2-(4-Methoxyphenyl)ethenyl]nicotinic Acid A mixture of NaH (60% dispersion in mineral oil, 7.4 g, 0.185 mole), tert-butanol (11.12 g, 0.15 mole), and anhydrous DMF (100 mL) was carefully warmed at 80° C. until gas evolution ceased, then was cooled to 0° C. under argon. A solution of ethyl 2-methylnicotinate (7.7 mL, 0.050 mole) in anhydrous DMF (17 mL) was added dropwise over 3 min, and the reddish-orange mixture was stirred at 0° C. for 1 hr. A solution of para-anisaldehyde (7.3 mL, 0.060 mL) in anhydrous DMF (17 mL) was added dropwise over 3 min, and the reaction was allowed to warm to RT. The mixture was stirred overnight, then was poured into ice water (200 mL), and the solution was acidified to pH 6 with glacial acetic acid. The volume was adjusted to 1 L with H$_2$O, the flask was scratched with a glass rod, and the mixture was allowed to stand at RT for several hr, then in the refrigerator overnight. The solid was collected by suction filtration and washed with H$_2$O. Recrystallization from boiling absolute EtOH gave the title compound (5.31 g, 42%, two crops) as yellow needles: $^1$H NMR (250 MHz, DMSO-d$_6$) δ 8.70 (dd, J=4.6, 1.7 Hz, 1H), 8.18 (dd, J=7.9, 1.7 Hz, 1H), 7.95 (d, J=15.8 Hz, 1H), 7.83 (d, J=15.8 Hz, 1H), 7.57 (d, J=8.7 Hz, 2H), 7.34 (dd, J=7.9, 4.6 Hz, 1H), 6.99 (d, J=8.7 Hz, 2H), 3.79 (s, 3H); MS (ES) m/e 256 (M+H)$^+$.

b) 2-[2-(4-Methoxyphenyl)ethyl]nicotinic Acid

10% Pd/C (2.21 g, 2.08 mmole) was added to a solution of 2-[2-(4-methoxyphenyl)ethenyl]nicotinic acid (5.31 g, 20.80 mmole) and 1.0 N NaOH (23 mL, 23 mmole) in H$_2$O (81 mL), and the mixture was shaken at RT under H$_2$ (50 psi) on a Parr apparatus. After 4.5 hr, the mixture was filtered through celite®, and the filtrate was acidified to pH 5 with glacial acetic acid. The solid was collected by suction filtration, washed with H$_2$O, and dried in high vacuum at 45° C. to afford the title compound (4.50 g, 84%) as an off-white solid: $^1$H NMR (400 MHz, DMSO-d$_6$) δ 8.65 (dd. J=4.7, 1.7 Hz, 1H), 8.15 (dd, J=7.8, 1.7 Hz, 1H), 7.35 (dd, J=7.8, 4.7 Hz, 1H), 7.13 (d, J=8.5 Hz, 2H), 6.84 (d, J=8.5 Hz, 2H), 3.71 (s, 3H), 3.25–3.40 (m, 2H), 2.82–2.93 (m, 2H).

Preparation 3

Preparation of 2-Bromo-N-methyl-N-[(1-methyl-1H-indol-2-yl)methyl]benzamide a) 2-Bromo-N-methyl-N-[(1-methyl-1H-indol-2-yl)methyl]benzamide—Method I A solution of 2-bromobenzoyl chloride (1.85 g, 8.45 mmole) in CH$_2$Cl$_2$ (10 mL) was added dropwise to a solution of 1-methyl-2-(methylaminomethyl)indole (1.47 g, 8.45 mmole) and Et$_3$N (3.6 mL, 25.8 mmole) in CH$_2$Cl$_2$ (50 mL) at 0° C. The reaction was stirred at 0° C. for 15 min, then was allowed to warm to RT. After 2 hr, the mixture was concentrated in vacuo, and the residue was diluted with H$_2$O. The mixture was extracted with Et$_2$O, and the combined Et$_2$O layers were dried (MgSO$_4$) and concentrated in vacuo. The oily residue was triturated with Et$_2$O/petroleum ether to afford the title compound (2.6 g, 87%) as a white solid: MS (ES) m/e 357 (M+H)$^+$.

b) 2-Bromo-N-methyl-N-[(1-methyl-1H-indol-2-yl)methyl]benzamide—Method II

EDC (660 mg, 3.44 mmole) was added to a solution of 2-bromobenzoic acid (693 mg, 3.45 mmole), 1-methyl-2-(methylaminomethyl)indole (600 mg, 3.45 mmole), and HOBt.H$_2$O (466 mg, 3.45 mmole) in DMF at RT. The reaction was stirred overnight, then was concentrated in vacuo. The residue was diluted with 5% NaHCO$_3$ and extracted with CH$_2$Cl$_2$. The combined organic extracts were washed with brine and dried over MgSO$_4$. Flash chromatography on silica gel (2% MeOH/CH$_2$Cl$_2$) gave the title compound (750 mg, 63%): MS (ES) m/e 357 (M+H)$^+$.

Preparation 4

Preparation of 1-Methyl-3-(methylaminomethyl)-1H-indazole a) Methyl 1-Methyl-1H-indazole-3-carboxylate Indazole-3-carboxylic acid (5.0 g, 30 mmole), K$_2$CO$_3$ (12.4 g, 90 mmole), and MeI (9.3 mL, 150 mmole) were combined in dry DMF (100 mL) and heated to 50° C. After 18 hr the mixture was cooled to RT and concentrated in vacuo. The residue was taken up in EtOAc and filtered, and the filtrate was concentrated under reduced pressure. The residue was flash chromatographed on silica gel (25% EtOAc/hexanes) to give the title compound (3.88 g, 68%) as a yellow solid: $^1$H NMR (300 MHz, CDCl$_3$) δ 8.24 (m, 1H), 7.47 (m, 2H), 7.34 (m, 1H), 4.19 (s, 3H), 4.05 (s, 3H).

b) N,1-Dimethyl-1H-indazole-3-carboxamide

A suspension of methyl 1-methyl-1H-indazole-3-carboxylate (3.88 g, 20.4 mmole) in 40% aqueous CH$_3$NH$_2$ (100 mL) and MeOH (5 mL) was stirred at RT for 4 hr, during which time a homogeneous solution formed. The solution was concentrated to approximately ⅓ volume and the precipitated solid was collected by filtration, washed with $H_2O$, and dried in vacuo to give the title compound (3.42 g. 89%) as a pale yellow solid: $^1$H NMR (300 MHz, $CDCl_3$) δ 8.24 (m, 1H), 7.47 (m, 2H), 7.34 (m, 1H), 6.95 (br s, 1H), 4.19 (s, 3H), 3.05 (d, J=12.0 Hz, 3H).

c) 1-Methyl-3-(methylaminomethyl)-1H-indazole

A solution of $LiAlH_4$ in THF (1.0 M, 36 mL, 36 mmole) was added slowly to a solution of N,1-dimethyl-1H-indazole-3-carboxamide (3.42 g, 18 mmole) in dry THF (90 mL) at RT. After 2 hr the mixture was heated to a gentle reflux. After 4 hr the mixture was cooled to RT and quenched by dropwise addition of 2.0 M NaOH until a white solid had formed. The mixture was dried ($MgSO_4$) and filtered, and the filtrate was concentrated under reduced pressure to give the title compound (3.28 g, 100%) as an oil: MS (ES) m/e 176 $(M+H)^+$.

Preparation 5
Preparation of 4-Amino-2-phenoxybenzoic Acid Hydrochloride a) 2-Phenoxy-4-nitrobenzoic Acid To a stirred solution of 2-chloro-4-nitrobenzoic acid (3 g, 14.9 mmole) and phenol (3 g, 31.9 mmole) in MeOH (20 mL) was added a solution of NaOMe in MeOH (25 wt %, 9 mL, 39.4 mmole). After 15 minutes the solution was concentrated to dryness and the residue was taken up in dimethylacetamide (50 mL). Copper powder (100 mg) was added and the mixture was heated at reflux with stirring (180° C. oil bath). After 1 hr the reaction was cooled to RT, acidified with 1.0 N HCl (40 mL), and extracted with EtOAc. The combined organic layers were washed with brine, dried ($MgSO_4$), and concentrated under vacuum. The remaining residue was triturated with 1:1 $Et_2O$/petroleum ether and dried under vacuum to afford the title compound (4.65 g). This was used without further purification.

b) 4-Amino-2-phenoxybenzoic Acid Hydrochloride

Crude 2-phenoxy-4-nitrobenzoic acid (4.65 g) was taken up in MeOH (150 mL) and hydrogenated at 50 psi $H_2$ over 10% Pd/C (1 g, 0.9 mmole) in a Parr apparatus. After 4 hr, the mixture was cooled to RT and filtered through a pad of celite®. The filtrate was acidified with 1.0 N HCl (20 mL), concentrated to dryness, and re-concentrated from MeOH (2x). The residue was triturated with EtOAc/$Et_2O$ and dried under vacuum to give the title compound (4.17 g, 100%) as a beige solid: MS (ES) m/e 230.2 $(M+H)^+$. This residue was used without further purification (89% pure by HPLC).

Preparation 6
Preparation of 2-(3-Acetamidophenoxy)benzoic Acid a) Methyl 2-(3-Acetamidophenoxy)benzoate To a stirred solution of methyl 2-iodobenzoate (10 g, 38.2 mmole) in dimethylacetamide (50 mL) was added 3-acetamidophenol (5 g, 33 mmole) and copper(I) oxide (2.5 g, 17 mmole), and the mixture was heated at reflux under argon (180° C. oil bath). After 24 h the reaction was cooled to RT and most of the solvent was distilled off. The remaining residue was purified by flash chromatography on silica gel (50% EtOAc/hexane) to give the crude title compound (4.95, 55%): MS (ES) m/e 286.2 $(M+H)^+$. The title compound prepared in this way contained approximately 45% N,O-diarylated acetamidophenol as a contaminant: MS (ES) m/e 420.4 $(M+H)^+$. The mixture was used without further purification.

b) 2-(3-Acetamidophenoxy)benzoic Acid

To a stirred solution of methyl 2-(3-acetamidophenoxy) benzoate (4.7 g crude mixture) in dioxane (100 mL) was added 1.0 N NaOH (24 mL). After stirring at RT for 72 hr the reaction was acidified with 1.0 N HCl (24 mL) and extracted with EtOAc. The combined organic layers were washed with brine, dried (Mg $SO_4$), and concentrated. The residue was purified by flash chromatography on silica gel (95:4:1 $CHCl_3$/MeOH/AcOH) to give the crude title compound (2.2 g, 34%) as a beige solid: MS (ES) m/e 272.2 $(M+H)^+$. The title compound prepared in this way contained approximately 46% of the diacid resulting from the di-ester starting material contaminant: MS (ES) m/e 392.2 $(M+H)^+$. The mixture was used without further purification.

Preparation 7
Preparation of 2-(Aminomethyl)-1-methylindole a) 1-Methylindole-2-carboxamide To a solution of 1-methylindole-2-carboxylic acid (5.0 g, 28.5 mmole) in THF (100 mL) at 0° C. was added N-methylmorpholine (3.5 mL, 31.8 mmole) followed by isobutyl chloroformate (4.0 mL, 30.8 mmole) dropwise over 5 minutes. A thick slurry formed quickly. The mixture was stirred for 30 min, then conc. $NH_4OH$ (4.0 mL. 58 mmole) was added in one portion with vigorous stirring, and the cooling bath was removed. The reaction was stirred at RT for 4 hr then was concentrated to dryness. The residue was triturated with 1.0 N $Na_2CO_3$ (50 mL), filtered, washed with a small volume of cold water, and dried under vacuum to give the title compound (2.46 g, 50%) as a white solid: Silica gel TLC (5% MeOH/$CHCl_3$) $R_f$ 0.50.

b) 2-(Aminomethyl)-1-methylindole

According to the procedure of Preparation 1(c), except substituting 1-methylindole-2-carboxamide (5.0 g, 30 mmole) for N,1-dimethylindole-2-carboxamide, the title compound (4.15 g, 86%) was prepared as an oil which solidified in the freezer: MS (ES) m/e 161.2 $(M+H)^+$.

Preparation 8
Preparation of 5-Amino-2-bromo-N-methyl-N-(1-methyl-1H-indol-2-ylmethyl)benzamide a) 5-Amino-2-bromobenzoic Acid Hydrochloride To a stirred solution of 2-bromo-5-nitrobenzoic acid (2.5 g, 10 mmole) in AcOH (75 mL) was added zinc powder (4.6 g, 70 mmole) portionwise. The reaction was exothermic. The mixture was stirred at RT for 16 hr then was filtered through a pad of celite®, and the filter pad was rinsed with a small volume of AcOH. The filtrate was concentrated under vacuum and the residue was dissolved in 1.0 N HCl (20 mL). The solution was concentrated to dryness, and the residue was triturated with $Et_2O$ and dried under vacuum to give the title compound (0.67 g, 27%) as an off-white solid: MS (ES) m/e 216.2 $(M+H)^+$.

b) 5-Amino-2-bromo-N-methyl-N-(1-methyl-1H-indol-2-ylmethyl)benzamide

According to the procedure of Preparation 3(b), except substituting 5-amino-2-bromobenzoic acid hydrochloride (0.67 g, 2.7 mmole) for 2-bromobenzoic acid, the title compound (0.62 g, 63%) was obtained as a white solid after flash chromatography on silica gel (70–80% EtOAc/hexanes): MS (ES) m/e 372.0 $(M+H)^+$.

The following examples illustrate methods for preparing the biologically active compounds of this invention from intermediate compounds such as those described in the foregoing Preparations.

Example 1
Preparation of 2-[2-(4-Methoxyphenyl)ethyl]-N-methyl-N-[(1-methyl-1H-indol-2-yl)methyl]nicotinamide a) 2-[2-(4-Methoxyphenyl)ethyl]-N-methyl-N-[(1-methyl-1H-indol-2-yl)methyl]nicotinamide EDC (0.60 g, 3.16 mmole) was added to a solution of 2-[2-(4-methoxyphenyl)ethyl]nicotinic acid (0.81 g, 3.16 mmole), 1-methyl-2-(methylaminomethyl)indole (0.50 g, 2.87 mmole), HOBt.H$_2$O (0.43 g, 3.16 mmole), and diisopropylethylamine (0.55 mL, 3.16 mmole) in DMF (15 mL) at RT. The reaction was stirred overnight, then was diluted with H$_2$O and extracted with EtOAc. Drying (Na$_2$SO$_4$), concentration, and flash chromatography on silica gel (5% MeOH/CHCl$_3$) gave the title compound (1.07 g, 90%) as a viscous yellow oil: $^1$H NMR (300 MHz, DMSO-d$_6$) δ 8.63 (m, 1H), 7.22–7.61 (m, 8H), 6.97 (d, J=8.1 Hz, 1H), 6.63 (d, J=8.1 Hz, 1H), 6.52 (s, 1H), 3.80 (s, 3H), 3.78 (m, 2H), 3.72 (s, 2H), 3.16 (m, 2H), 3.03 (s, 3H), 2.57 (s, 3H), MS (ES) m/e 414 (M+H)$^+$. Anal. Calcd for C$_{26}$H$_{27}$N$_3$O$_2$: C, 75.52; H, 6.58: N, 10.16. Found C, 75.84; H, 6.68; N, 9.76.

Example 2

Preparation of N-Methyl-N-[(1-methyl-1H-indol-2-yl)methyl]-2-phenylbenzamide a) N-Methyl-N-[(1-methyl-1H-indol-2-yl)methyl]-2-phenylbenzamide EDC (0.22 g, 1.14 mmole) was added to a solution of 2-biphenylcarboxylic acid (0.22 g, 1.14 mmole), 1-methyl-2-(methylaminomethyl)indole (0.20 g, 1.15 mmole), and HOBt.H$_2$O (0.15 g, 1.11 mmole) in DMF (20 mL) at RT. The reaction was stirred overnight, then was concentrated in vacuo. The residue was diluted with 5% NaHCO$_3$ and extracted with CH$_2$Cl$_2$. The combined organic extracts were washed with brine and dried over MgSO$_4$. Flash chromatography on silica gel (3% MeOH/CH$_2$Cl$_2$) followed by preparative TLC (3% MeOH/CH$_2$Cl$_2$) gave the title compound (0.10 g, 25%) as a light yellow solid: $^1$H NMR (360 MHz, CDCl$_3$) indicated an approximately 5:1 mixture of amide rotamers; for the major rotamer: δ 7.03–7.58 (m, 13H), 6.19 (s, 1H), 4.50 –5.00 (m, 2H), 3.57 (s, 3H), 2.40 (s, 3H); for the minor rotamer: δ 7.03–7.58 (m, 13H), 6.14 (s, 1H), 4.50–5.00 (m, 2H), 3.38 (s, 3H), 2.76 (s, 3H); MS (ES) m/e 356 (M+H)$^+$. Anal. Calcd for C$_{24}$H$_{22}$N$_2$O.0.80H$_2$O: C, 78.15; H, 6.45; N, 7.59. Found: C, 77.96; H, 6.29; N, 7.35.

Example 3

Preparation of N-methyl-N-[(1-methyl-1H-indol-2-yl)methyl]-2-(pyridin-4-yl)benzamide a) N-methyl-N-[(1-methyl-1H-indol-2-yl)methyl]-2-(pyridin-4-yl)benzamide A solution of 2-bromo-N-methyl-N-[(1-methyl-1H-indol-2-yl)methyl]benzamide (0.30 g, 0.84 mmole), pyridine-4-boronic acid (0.20 g, 1.63 mmole), tetrakis(triphenylphosphine)palladium(0) (29 mg, 0.025 mmole), and Cs$_2$CO$_3$ (1.10 g, 3.38 mmole) in 10:1 DME/H$_2$O (25 mL) was degassed, then was heated under N$_2$ overnight. The resulting mixture was concentrated in vacuo, and the residue was taken up in 10% NaOH solution. The mixture was extracted with CH$_2$Cl$_2$, and the combined organic extracts were washed with brine and dried (MgSO$_4$). Flash chromatography on silica gel (3% MeOH/CH$_2$Cl$_2$) followed by preparative TLC (3% MeOH/CH$_2$Cl$_2$) gave the title compound (98 mg, 33%) as a white solid: $^1$H NMR (300 MHz, CDCl$_3$) indicated an approximately 5:1 mixture of amide rotamers; for the major rotamer: δ 8.50–8.65 (m, 2H), 7.00–7.60 (m, 10H), 6.27 (s, 1H), 4.50–5.00 (m, 2H), 3.62 (s, 3H), 2.49 (s, 3H); for the minor rotamer: δ 8.65–8.75 (m, 2H), 7.00–7.60 (m, 10H), 6.12 (s, 1H), 4.50–5.00 (m, 2H), 3.41 (s, 3H), 2.86 (s, 3H); MS (ES) m/e 356 (M+H)$^+$. Anal. Calcd for C$_{23}$H$_{21}$N$_3$O.0.10H$_2$O: C, 77.33; H, 5.98; N, 11.76. Found: C, 77.07; H, 5.98; N, 11.56.

Example 4

Preparation of N-Methyl-N-[(1-methyl-1H-indol-2-yl)methyl-]2-(pyridin-3-yl)benzamide a) N-Methyl-N-[(1-methyl-1H-indol-2-yl)methyl]-2-(pyridin-3-yl)benzamide According to the procedure of Example 3(a), except substituting pyridine-3-boronic acid (173 mg, 1.41 mmole) for the pyridine-4-boronic acid, the title compound (56 mg, 22%) was obtained as a light yellow foam after flash chromatography on silica gel (3% MeOR/CH$_2$Cl$_2$) followed by preparative TLC (3% MeOH/CH$_2$Cl$_2$): $^1$H NMR (360 MHz, CDCl$_3$) indicated an approximately 5:1 mixture of amide rotamers. for the major rotamer: δ 8.68 (br s, 1H), 8.50 (br s, 1H), 7.71–7.77 (m, 1H), 7.63–7.72 (m, 1H), 7.31–7.57 (m, 4H), 7.04–7.31 (m, 4H), 6.23 (s, 1H), 4.60–4.85 (m, 2H), 3.63 (s, 3H), 2.48 (s, 3H); for the minor rotamer: δ 8.74 (br s, 1H), 8.68 (br s, 1H), 7.85–7.89 (m, 1H), 7.31–7.57 (m, 5H), 7.04–7.31 (m, 4H), 6.17 (s, 1H), 4.30–4.45 (m, 2H), 3.40 (s, 3H), 2.82 (s, 3H); MS (ES) m/e 356 (M+H)$^+$.

Example 5

Preparation of N-Methyl-N-[(1-methyl-1H-indol-2-yl)methyl]-2-(thiophen-3-yl)benzamide a) N-Methyl-N-[(1-methyl-1H-indol-2-yl)methyl]-2-(thiophen-3-yl)benzamide According to the procedure of Example 3(a), except substituting thiophene-3-boronic acid (179 mg, 1.40 mmole) for the pyridine-4-boronic acid the title compound (100 mg, 40%) was obtained following flash chromatography on silica gel (20% EtOAc/hexanes): $^1$H NMR (360 MHz, CDCl$_3$) indicated an approximately 4:1 mixture of amide rotamers; for the major rotamer: δ 7.00–7.56 (m, 11H), 6.28 (s, 1H), 4.95–5.15 (m, 1H), 4.48–4.68 (m, 1H), 3.69 (s, 3H), 2.41 (s, 3H); for the minor rotamer: δ 7.00–7.56 (m, 11H), 6.15 (s, 1H), 4.38 (d, J=15.5 Hz, 1H), 3.65 (d, J=15.5 Hz, 1H), 3.60 (s, 3H), 2.84 (s, 3H); MS (ES) m/e 361 (M+H)$^+$. Anal. Calcd for C$_{22}$H$_{20}$N$_2$OS.0.10H$_2$O: C, 72.94; H, 5.62; N, 7.73. Found: C, 72.70; H, 5.58; N, 7.46.

Example 6

Preparation of N-Methyl-N-[(1-methyl-1H-indol-2-yl)methyl]-2-(furan-3-yl)benzamide a) N-Methyl-N-[(1-methyl-1H-indol-2-yl)methyl]-2-(furan-3-yl)benzamide According to the procedure of Example 3(a), except substituting furan-3-boronic acid (156 mg, 1.39 mmole) for the pyridine-4-boronic acid, the title compound (100 mg, 41%) was obtained after preparative TLC (20% EtOAc/hexanes) followed by flash chromatography on silica gel (20% EtOAc/hexanes): $^1$H NMR (360 MHz, CDCl$_3$) indicated an approximately 3.5:1 mixture of amide rotamers; for the major rotamer: δ 7.61–7.65 (m, 1H), 7.03–7.58 (m, 9H), 6.55–6.58 (m, 1H), 6.37 (s, 1H), 5.07–5.27 (m, 1H), 4.58–4.68 (m, 1H), 3.74 (s, 3H), 2.50 (s, 3H); for the minor rotamer: δ 7.68–7.71 (m, 1H), 7.03–7.58 (m, 9H), 6.63–6.66 (m, 1H), 6.24 (s, 1H), 4.42 (d, J=15.7 Hz, 1H), 3.97 (d, J=15.7 Hz, 1H), 3.39 (s, 3H), 2.94 (s, 3H); MS (ES) m/e 345 (M+H)$^+$. Anal. Calcd for C$_{22}$H$_{20}$N$_2$O$_2$.0.10H$_2$O: C, 76.32; H, 5.88; N, 8.09. Found: C, 76.11; H, 5.94; N, 7.79.

Example 7

Preparation of N-Methyl-N-[(1-methyl-1H-indol-2-yl)methyl]-2-phenoxybenzamide a) N-Methyl-N-[(1-methyl-1H-indol-2-yl)methyl]-2-phenoxybenzamide EDC (230 mg, 1.2 mmole) was added to a solution of 2-phenoxybenzoic acid (214.2 mg, 1.0 mmole), 1-methyl- 2-(methylaminomethyl)indole (209.1 mg, 1.2 mmole), HOBt.H$_2$O (162.2 mg, 1.2 mmole), and triethylamine (0.35 mL, 2.5 mmole) in DMF (5 mL) at RT. After 16.5 hr, the reaction was concentrated, and the residue was reconcentrated from xylenes/CHCl$_3$ to remove residual DMF. Flash chromatography on silica gel (40% EtOAc/hexanes) gave the title compound (393.5 mg, quantitative) as a nearly colorless, very viscous oil: $^1$H NMR (360 MHz, CDCl$_3$) indicated an approximately 5:1 mixture of amide rotamers; for the major rotamer: δ 7.56 (d, J=7.9 Hz, 1H), 6.98–7.50 (m, 9H), 6.95 (d, J=7.6 Hz, 2H), 6.87 (d, J=7.5 Hz, 1H), 6.49 (s, 1H), 4.40–5.40 (m, 2H), 3.62 (s, 3H), 2.84 (s, 3H); for the minor rotamer: δ 6.80–7.50 (m, 13H), 6.47 (s, 1H), 4.40–5.40 (m, 2H), 3.56 (s, 3H), 2.98 (s, 3H); MS (ES) m/e 371 (M+H)$^+$.

Example 8

Preparation of N,2-Dimethyl-N-[(1-methyl-1H-indol-2-yl)methyl]benzamide a) N,2-Dimethyl-N-[(1-methyl-1H-indol-2-yl)methyl]benzamide EDC (0.22 g, 1.15 mmole) was added to a solution of ortho-toluic acid (0.15 g, 1.10 mmole), 1-methyl-2-(methylaminomethyl)indole (0.20 g, 1.15 mmole), and HOBt.H$_2$O (0.15 g, 1.11 mmole) in DMF at RT. The reaction was stirred overnight, then was concentrated in vacuo. The residue was diluted with 5% NaHCO$_3$ and extracted with CH$_2$Cl$_2$. The combined organic extracts were washed with brine and dried over MgSO$_4$. Flash chromatography on silica gel (20% EtOAc/hexanes) gave a colorless gum, which was triturated with Et$_2$O to afford the title compound (0.2 g, 37%) as a white solid: $^1$H NMR (300 MHz, CDCl$_3$) indicated an approximately 5:1 mixture of amide rotamers; for the major rotamer: δ 7.60 (d, J=7.7 Hz, 1H), 7.05–7.40 (m, 7H), 6.52 (s, 1H), 5.01 (s, 2H), 3.85 (s, 3H), 2.71 (s, 3H), 2.30 (s, 3H); for the minor rotamer: δ 7.60 (d, J=7.7 Hz, 1H), 7.05–7.40 (m, 7H), 6.44 (s, 1H), 4.52 (s, 2H), 3.50 (s, 3H), 3.14 (s, 3H), 2.37 (s, 3H); MS (ES) m/e 293 (M+H)$^+$. Anal. Calcd for C$_{19}$H$_{20}$N$_2$O.0.35H$_2$O: C, 76.40; H, 6.99; N, 9.38. Found: C, 76.10; H, 6.83; N, 9.33.

Example 9

Preparation of 2-[3-(Acetylamino)phenyl]-N-methyl-N-[(1-methyl-1H-indol-2-yl)methyl]benzamide a) 2-[3-(Acetylamino)phenyl]-N-methyl-N-[(1-methyl-1H-indol-2-yl)methyl]benzamide According to the procedure of Example 3(a), except substituting 3-(acetylamino)phenylboronic acid (250 mg, 1.40 mmole) for the pyridine-4-boronic acid, the title compound (190 mg, 66%) was obtained after flash chromatography on silica gel (3% MeOH/CH$_2$Cl$_2$): $^1$H NMR (300 MHz, CDCl$_3$) indicated an approximately 4:1 mixture of amide rotamers; for the major rotamer: δ 7.00–7.80 (m, 12H), 6.20 (s, 1H), 4.65–4.90 (m, 2H), 3.54 (s, 3H), 2.52 (s, 3H), 2.04 (s, 3H); for the minor rotamer: δ 7.00–7.80 (m, 12H), 6.12 (s, 1H), 4.40 (d, J=15 Hz, 1H), 3.75 (d, J=15 Hz, 1H), 3.38 (s, 3H), 2.84 (s, 3H), 2.16 (s, 3H); MS (ES) m/e 412 (M+H)$^+$. Anal. Calcd for C$_{26}$H$_{25}$N$_3$O$_2$ 0.20 H$_2$O: C, 74.87; H, 6.42; N, 9.77. Found: C, 74.65; H, 6.36; N, 9.50.

Example 10

Preparation of N-methyl-N-(1-methyl-1H-indol-2-ylmethyl)-2-phenoxynicotinamide

According to the procedure of Example 7, except substituting 2-phenoxynicotinic acid (215.2 mg, 1.0 mmole) for the 2-phenoxybenzoic acid, the title compound (311.3 mg, 84%) was prepared as a white powder: 1H NMR (300 MHz, CDCl$_3$) indicated an approximately 5:1 mixture of amide rotamers; for the major rotamer: δ 8.19 (dd, J=5.0, 1.9 Hz, 1H), 7.77 (dd, J=7.3, 1.9 Hz, 1H), 7.57 (d, J=7.8 Hz, 1H), 7.00–7.45 (m, 9H), 6.54 (s, 1H), 4.50–5.60 (m, 2H), 3.74 (s, 3H), 2.89 (s, 3H); MS (ES) m/e 372 (M+H)$^+$.

Example 11

Preparation of N-Methyl-N-(1-methyl-1H-indazol-3-ylmethyl)-2-phenylbenzamide

A solution of 2-biphenylcarboxylic acid (198 mg, 1 mmole), 1-methyl-3-(methylaminomethyl)-1H-indazole (210 mg, 1.2 mmole), EDC (230 mg, 1.2 mmole), HOBt.H$_2$O (162 mg, 1.2 mmole), and triethylamine (0.28 mL, 2.0 mmole) in DMF (5 mL) was stirred at RT. After 18 hr, the reaction was concentrated to dryness, and the residue was purified by flash chromatography on silica gel (45% EtOAc/hexanes). The title compound (221 mg, 62%) was obtained as a white solid: MS (ES) m/e 356 (M+H)$^+$.

Example 12

Preparation of N-Methyl-N-(1-methyl-1H-indazol-3-ylmethyl)-2-phenoxybenzamide

According to the procedure of Example 11, except substituting 2-phenoxybenzoic acid (214 mg, 1 mmole) for the 2-biphenylcarboxylic acid, the title compound was prepared as a sticky solid: MS (ES) m/e 372 (M+H)$^+$.

Example 13

Preparation of 2-Methoxy-N-methyl-N-(1-methyl-1H-indol-2-ylmethyl)benzamide

According to the procedure of Preparation 3(a), except substituting 2-methoxybenzoyl chloride (0.25 g, 1.44 mmole) for the 2-bromobenzoyl chloride, the title compound (0.17 g, 39%) was prepared as a white solid: MS (ES) m/e 309 (M+H)$^+$.

Example 14

Preparation of 2,4-Dihydroxy-N-methyl-N-(1-methyl-1H-indol-2-ylmethyl)benzamide

According to the procedure of Example 1, except substituting 2,4 dihydroxybenzoic acid (0.18 g, 1.15 mmole) for the 2-biphenylcarboxylic acid the title compound (0.074 g, 21%) was prepared as a white solid: MS (ES) m/e 311 (M+H)$^+$.

Example 15

Preparation of 2-Dimethylamino-N-methyl-N-(1-methyl-1H-indol-2-ylmethyl)benzamide According to the procedure of Example 1, except substituting 2 dimethylaminobenzoic acid (0.2 g, 1.15 mmole) for the 2-biphenylcarboxylic acid, the title compound (0.10 g, 28%) was prepared as a white solid: MS (ES) m/e 322 (M+H)$^+$.

Example 16

Preparation of N-methyl-N-(1-methyl-1H-indol-2-ylmethyl)-2-(piperidin-1-yl)benzamide According to the procedure of Example 1, except substituting 2-piperidinobenzoic acid (0.23 g, 1.15 mmole) for the 2-biphenylcarboxylic acid, the title compound (0.10 g, 24%) was prepared as a white solid: MS (ES) m/e 362 (M+H)$^+$.

Example 17

Preparation of N-methyl-N-(1-methyl-1H-indol-2-ylmethyl)-2-(trifluoromethyl)benzamide According to the procedure of Preparation 1(a), except substituting 2 (trifluoromethyl)benzoyl chloride (0.24 g, 1.15 mmole) for the 2-bromobenzoyl chloride, the title compound (0.10 g, 25%) was prepared as a white solid: MS (ES) m/e 347 (M+H)+.

Example 18
Preparation of 4-Amino-N-methyl-N-(1-methyl-1H-indol-2-ylmethyl)-2-phenoxybenzamide To 4-amino-2-phenoxybenzoic acid hydrochloride (1.0 g, 3.4 mmole) in 1:1 DMF/CH$_2$Cl$_2$ (75 mL) was added 1-methyl-2-(methylaminomethyl)indole (0.61 g, 3.5 mmole), HOBt.H$_2$O (0.47 g, 3.5 mmole), Et$_3$N (1.0 mL, 7.1 mmole), then EDC (0.67 g, 3.5 mmole). The reaction was stirred at RT for 16 hr then was concentrated under vacuum. The residue was taken up in EtOAc (200 mL) and the solution was washed with water, dried (Na$_2$SO$_4$), and concentrated. Flash chromatography on silica gel (2% MeOH/CHCl$_3$, then rechromatography using 70% EtOAc/hexanes) gave the title compound (0.62 g, 42%) as a white solid: MS (ES) m/e 386.2 (M+H)+.

Example 19
Preparation of 2-[3-(Acetylamino)phenoxy]-N-methyl-N-(1-methyl-1H-indol-2-ylmethyl)benzamide According to the procedure of Example 18, except substituting 2-(3-acetamidophenoxy)benzoic acid (1.0 g, crude mixture) for the 4-amino-2-phenoxy benzoic acid hydrochloride, the title compound (0.36 g) was prepared as an off-white solid: MS (ES) m/e 428.2 (M+H)+. The bis-coupled product (0.62 g) from the starting diacid contaminant was also isolated: MS (ES) m/e 703.32 (M+H)+.

Example 20
Preparation of 2-[3-(Acetylamino)phenyl]-N-methyl-N-(1-methyl-1H-indol-3-ylmethyl)benzamide a) 2-Bromo-N-(1-methyl-1H-indol-2-ylmethyl)benzamide According to the procedure of Preparation 3(b), except substituting 2-(aminomethyl)-1-methylindole (1.0 g, 6.2 mmole) for 1-methyl-2-(methylaminomethyl)indole, the title compound (1.10 g, 64%) was obtained: $^1$H NMR (400 MHz, DMSO-d$_6$) δ 8.97 (t, 1H), 7.65 (d, J=7.9 Hz, 1H), 7.49 (d, J=7.8 Hz, 1H), 7.41–7.46 (m, 3H), 7.36 (m, 1H), 7.12 (t, 1H), 7.00 (t, 1H), 6.44 (s, 1H), 4.65 (d, J=5.6 Hz, 2H), 3.77 (s, 3H); MS (ES) m/e 343.0 (M+H)+.

b) 2-[3-(Acetylamino)phenyl]-N-methyl-N-(1-methyl-1H-indol-3-ylmethyl)benzamide

According to the procedure of Example 9, except substituting 2-bromo-N-(1-methyl-1H-indol-2-ylmethyl)benzamide (1 g, 2.9 mmole) for 2-bromo-N-methyl-N-(1-methyl-1H-indol-2-ylmethyl)benzamide, the title compound (1.12 g, 100%) was obtained after flash chromatography on silica gel (70–90% EtOAc/hexanes): MS (ES) m/e 398.2 (M+H)+.

Example 21
Preparation of 2-[3-(Acetylamino)phenyl]-5-amino-N-methyl-N-(1-methyl-1H-indol-3-ylmethyl)benzamide According to the procedure of Example 9, except substituting 5-amino-2-bromo-N-methyl-N-(1-methyl-1H-indol-2-ylmethyl)benzamide (0.62 g, 1.7 mmole) for 2-bromo-N-methyl-N-(1-methyl-1H-indol-2-ylmethyl)benzamide, the title compound (0.47g, 65%) was obtained after flash chromatography on silica gel (EtOAc): MS (ES) m/e 421.2 (M+H)+.

Example 22
Parenteral Dosage Unit Composition

A preparation which contains 20 mg of the compound of Example 1 as a sterile dry powder is prepared as follows: 20 mg of the compound is dissolved in 15 mL of distilled water. The solution is filtered under sterile conditions into a 25 mL multi-dose ampoule and lyophilized. The powder is reconstituted by addition of 20 mL of 5% dextrose in water (D5W) for intravenous or intramuscular injection. The dosage is thereby determined by the injection volume. Subsequent dilution may be made by addition of a metered volume of this dosage unit to another volume of D5W for injection, or a metered dose may be added to another mechanism for dispensing the drug, as in a bottle or bag for IV drip infusion or other injection-infusion system.

Example 23
Oral Dosage Unit Composition

A capsule for oral administration is prepared by mixing and milling 50 mg of the compound of Example 1 with 75 mg of lactose and 5 mg of magnesium stearate. The resulting powder is screened and filled into a hard gelatin capsule.

Example 24
Oral Dosage Unit Composition

A tablet for oral administration is prepared by mixing and granulating 20 mg of sucrose, 150 mg of calcium sulfate dihydrate and 50 mg of the compound of Example 1 with a 10% gelatin solution. The wet granules are screened, dried, mixed with 10 mg starch, 5 mg talc and 3 mg stearic acid; and compressed into a tablet.

The above description fully discloses how to make and use the present invention. However, the present invention is not limited to the particular embodiments described hereinabove, but includes all modifications thereof within the scope of the following claims. The various references to journals, patents and other publications which are cited herein comprises the state of the art and are incorporated herein by reference as though fully set forth.

What is claimed is:

1. A compound according to formula (I) or (II):

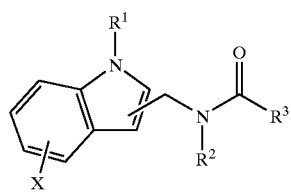
(I)

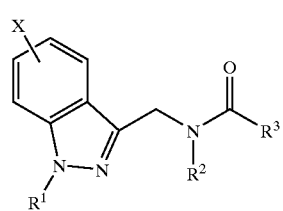
(II)

wherein:

$R^1$ is H or $C_{1-4}$alkyl;
$R^2$ is $C_{1-4}$alkyl;
$R^3$ is

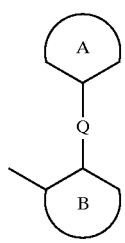 or 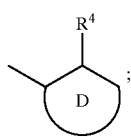;

Q is a single bond, —O—, —S—, —NH—, —CH$_2$—, or —CH$_2$CH$_2$—;

$R^4$ is $C_{1-6}$alkyl, $OC_{1-6}$alkyl, OH, $CF_3$ or piperidinyl;

is a five- or six-membered heteroaromatic ring or a six-membered aromatic ring unsubstituted or substituted by $R^5$;

is a five- or six-membered heteroaromatic ring or a six-membered aromatic ring unsubstituted or substituted by $R^6$;

is a five- or six-membered heteroaromatic ring or a six-membered aromatic ring unsubstituted or substituted by $R^6$;

$R^5$ is OR' or NR'C(O)R';
$R^6$ is OR' or N(R')$_2$;

X is H, $C_{1-4}$alkyl, OR', SR', CN, N(R')$_2$, CH$_2$N(R')$_2$, NO$_2$, CF$_3$, CO$_2$R', CON(R')$_2$, COR', NR'C(O)R', F, Cl, Br, I or —S(O)$_r$CF$_3$;

R' is H, $C_{1-6}$alkyl or —C$_{0-6}$alkyl-Ar; and r is 0, 1 or 2;

or a pharmaceutically acceptable salt thereof.

2. A compound according to claim 1 of formula (Ia):

(Ia)

3. A compound according to claim 1 in which R³ is:

4. A compound according to claim 3 in which is 2-, 3- or 4-pyridyl, 2- or 3-furanyl, 2- or 3-thiophenyl, thiazolyl, phenyl or phenyl substituted by $OC_{1-4}$alkyl or $NHC(O)C_{1-4}$alkyl.

5. A compound according to claim 4 in which is 3- or 4-pyridyl, 3-furanyl, 3-thiophenyl, phenyl or phenyl substituted by $OCH_3$ or $NHC(O)CH_3$.

6. A compound according to claim 3 in which is 2-, 3- or 4-pyridyl, phenyl or phenyl substituted by OH or $NH_2$.

7. A compound according to claim 6 in which is phenyl or 2-pyridyl.

8. A compound according to claim 3 in which Q is a single bond.

9. A compound according to claim 3 in which Q is —O— or —$CH_2$—.

10. A compound according to claim 1 in which R³ is:

11. A compound according to claim 10 in which is phenyl unsubstituted or substituted by OH, $NH_2$ or $N(CH_3)_2$ and R⁴ is $C_{1-4}$alkyl, $OC_{1-4}$alkyl, OH, $CF_3$, or piperidinyl.

12. A compound according to claim 1 of formula (IIa):

(IIa)

13. A compound according to claim 1 which is:

2-[2-(4-Methoxyphenyl)ethyl]-N-methyl-N-[(1-methyl-1H-indol-2-yl)methyl]nicotinamide;

N-Methyl-N-[(1-methyl-1H-indol-2-yl)methyl]-2-phenylbenzamide;

N-Methyl-N-[(1-methyl-1H-indol-2-yl)methyl]-2-(pyridin-4-yl)benzamide;

N-Methyl-N-[(1-methyl-1H-indol-2-yl)methyl]-2-(pyridin-3-yl)benzamide;

N-Methyl-N-[(1-methyl-1H-indol-2-yl)methyl]-2-(thiophen-3-yl)benzamide;

N-Methyl-N-[(1-methyl-1H-indol-2-yl)methyl]-2-(furan-3-yl)benzamide;

N-Methyl-N-[(1-methyl-1H-indol-2-yl)methyl]-2-phenoxybenzamide;

N,2-Dimethyl-N-[(1-methyl-1H-indol-2-yl)methyl]benzamide;

2-[3-(Acetylamino)phenyl]-N-methyl-N-[(1-methyl-1H-indol-2-yl)methyl]benzamide;

2-methoxy-N-methyl-N-(1-methyl-1H-indol-2-ylmethyl)benzamide;

2,4-dihydroxy-N-methyl-N-(1-methyl-1H-indol-2-ylmethyl)benzamide;

2-dimethylamino-N-methyl-N-(1-methyl-1H-indol-2-ylmethyl)benzamide;

N-methyl-N-(1-methyl-1H-indol-2-ylmethyl)-2-(piperidin-1-yl)benzamide;

N-methyl-N-(1-methyl-1H-indol-2-ylmethyl)-2-(trifluoromethyl)benzamide;

4-amino-N-methyl-N-(1-methyl-1H-indol-2-ylmethyl)-2-phenoxybenzamide;

N-methyl-N-(1-methyl-1H-indol-2-ylmethyl)-2-phenoxynicotinamide;

N-methyl-N-(1-methyl-1H-indazol-3-ylmethyl)-2-phenylbenzamide;

N-methyl-N-(1-methyl-1H-indazol-3-ylmethyl)-2-phenoxybenzamide;

2-[3-(acetylamino)phenoxy]-N-methyl-N-(1-methyl-1H-indol-2-ylmethyl)-benzamide;

2-[3-(acetylamino)phenyl]-N-methyl-N-(1-methyl-1H-indol-3-ylmethyl)-benzamide; or 2-[3-(acetylamino)phenyl]-5-amino-N-methyl-N-(1-methyl-1H-indol-3-ylmethyl)benzamide;

or a pharmaceutically acceptable salt thereof.

14. A pharmaceutical composition which comprises a therapeutically effective amount of a compound according to claim 1 and a pharmaceutically acceptable carrier.

15. A method for inhibiting FabI which comprises administering to a subject in need thereof a therapeutically effective amount of a compound according to claim 1.

16. A method of treating bacterial infections which comprises administering to a subject in need thereof a therapeutically effective amount of a compound according to claim 1.

17. A process for preparing compounds of formula (I) or (II) as defined in claim 1, which process comprises:

(i) reacting a compound of formula (III) with a compound of formula (IV):

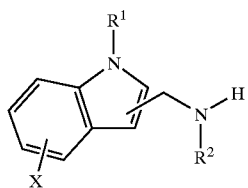

(III)

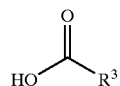

(IV)

wherein $R^1$, $R^2$, $R^3$ and X are as defined in formula (I), with any reactive functional groups protected, in the presence of EDC and HOBT; or (ii) reacting a compound of formula (V) with a compound of formula (IV):

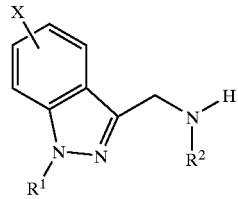

(V)

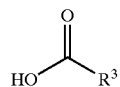

(IV)

wherein $R^1$, $R^2$, $R^3$ and X are as defined in formula (I), with any reactive functional groups protected, in the presence of EDC and HOBT;

and thereafter removing any protecting groups, and optionally forming a pharmaceutically acceptable salt.

* * * * *

SEQUENCE LISTING

<160> NUMBER OF SEQ ID NOS: 4

<210> SEQ ID NO 1
<211> LENGTH: 39
<212> TYPE: DNA
<213> ORGANISM: Home sapiens

<400> SEQUENCE: 1
cgcctcgaga tgttaaatct tgaaaacaaa acatatgtc                              39

```
<210> SEQ ID NO 2
<211> LENGTH: 33
<212> TYPE: DNA
<213> ORGANISM: Homo sapiens

<400> SEQUENCE: 2
cgcggatcca atcaagtcag gttgaaatat cca                       33

<210> SEQ ID NO 3
<211> LENGTH: 28
<212> TYPE: DNA
<213> ORGANISM: Home sapiens

<400> SEQUENCE: 3
catgggctta aatcttgaaa acaaaaca                             28

<210> SEQ ID NO 4
<211> LENGTH: 26
<212> TYPE: DNA
<213> ORGANISM: Home sapiens

<400> SEQUENCE: 4
tatgttttgt tttcaagatt taagcc                               26
```